United States Patent [19]

Nickel

[11] Patent Number: 5,776,859

[45] Date of Patent: Jul. 7, 1998

[54] SODIUM CHANNEL ACTIVE NOVEL COMPOUNDS AND RELATED PROCESSES AND BIOASSAY TECHNIQUES

[76] Inventor: Alfred A. Nickel, 3535 Spring Hill Rd., Lafayette, Calif. 94549

[21] Appl. No.: 559,215

[22] Filed: Nov. 15, 1995

[51] Int. Cl.⁶ .......................... A01N 43/10; A61K 31/38; C07D 333/20

[52] U.S. Cl. .............. 504/28; 514/447; 549/68; 549/69

[58] Field of Search .............. 549/68, 69, 59; 514/447, 326; 504/289, 248; 546/212

[56] References Cited

U.S. PATENT DOCUMENTS

| | | | |
|---|---|---|---|
| 3,855,243 | 12/1974 | Ruschig et al. | 260/332.2 |
| 3,963,750 | 6/1976 | Goudie | 549/68 |
| 4,006,218 | 2/1977 | Sipos | 424/54 |
| 4,069,105 | 1/1978 | Singh | 195/63 |
| 4,091,090 | 5/1978 | Sipos | 424/45 |
| 4,108,867 | 8/1978 | Baird et al. | 549/68 |
| 4,197,318 | 4/1980 | Sipos | 424/326 |
| 4,240,820 | 12/1980 | Dickore et al. | 549/68 |
| 4,321,257 | 3/1982 | Sipos | 424/80 |
| 4,438,046 | 3/1984 | Grew et al. | 260/501.15 |
| 4,474,748 | 10/1984 | Sipos | 424/40 |
| 4,562,060 | 12/1985 | Brobert et al. | 424/28 |
| 4,628,063 | 12/1986 | Haines et al. | 514/626 |
| 4,650,771 | 3/1987 | Buckler et al. | 436/536 |
| 4,659,714 | 4/1987 | Watt-Smith | 514/260 |
| 4,757,088 | 7/1988 | Haines et al. | 514/563 |
| 4,891,386 | 1/1990 | Gasparotti | 514/555 |
| 4,914,131 | 4/1990 | Haines et al. | 514/626 |
| 5,132,411 | 7/1992 | Egli et al. | 549/68 |
| 5,166,346 | 11/1992 | Rippel et al. | 544/146 |
| 5,276,032 | 1/1994 | King et al. | 514/239.2 |
| 5,292,767 | 3/1994 | Mita et al. | 549/68 |

FOREIGN PATENT DOCUMENTS

| | | |
|---|---|---|
| 889225 | 2/1962 | United Kingdom . |

OTHER PUBLICATIONS

Ruschig et al., 1969, Abstract entitled, "3–Aminoacylamino–Thiophens and Process for Preparing Them," *Patentjoernaal (Insluitende Handelsmerke En Modelle)*.

Nickel, A.A., *Aneth Prog*. 37:42–45 (1990).

Nickel, A.A., *Dentoalveolar Surgery* 5(1):17–24 (1993).

Bryant, et al., *Carcinogenesis* 15(10): 2287–2290; 1994.

National Toxicology Program No. 278, *NIH* Pub. No. 90–2534, Jan., 1990.

US Department of HHS, *Sixth Annual Report on Carcinogens, National Toxicology Program* vol. 2, pp. 775–777 (1991).

Hecht et al., *Cancer Lett*. 16:103–08 (1982).

Weisberger et al., *J. Environ. Pathol. Toxicol*. 2:325–56 (1978).

Beychok, S., *Science* 154: 1288–1289 (1966).

Sy and deMalleray, *Bull. Soc. Chim*., France (1963) at 1276.

Gever, *J. Am. Chem. Soc*. 77:577 (1955).

Mackay, *Can J. Chem*. 44:2881 (1966).

Ruschug et al., "Anesthetic 3–(aminoacylamino) thiophenes", CA:vol. 71, 91287d (S. African 6804265), 1969.

Ruschug et al. "3–Arylaminothiophene–4–Carboxylic Acid Aminoalkyl Ester", CA:vol. 82, 170659, 1975.

Farbwerke Hoechst A.G., "Antiphlogistic and Antipynetic Aminothiophene Derivatives", Neth. Appl. 6, 604, 742, CA: vol. 67, 218 i/P, 1967.

Kharizomenova et al., "Functional Derivatives of Thiophene", CA: vol. 95, 24681k, 1981.

*Primary Examiner*—Deborah Lambkin
*Attorney, Agent, or Firm*—Albert P. Halluin

[57] ABSTRACT

The present invention discloses novel sodium channel active compounds, processes for making such compounds, and the use of such compounds as local anesthetics and pesticides.

6 Claims, 2 Drawing Sheets

5,776,859

1

SODIUM CHANNEL ACTIVE NOVEL COMPOUNDS AND RELATED PROCESSES AND BIOASSAY TECHNIQUES

CROSS-REFERENCE TO RELATED APPLICATION

This application is related to application, Ser. No. 08/236,863, filed on Apr. 29, 1994, which is a file wrapper continuation of application, Ser. No. 07/900,422, filed on Jun. 18, 1992, now abandoned, which is a continuation-in-part of application, Ser. No. 07/782,605, filed on Nov. 25, 1991, now also abandoned. Each of the above-referenced applications is incorporated by reference herein in its entirety.

INTRODUCTION

The present invention relates to sodium channel active organic compounds, their uses, and processes for making such compounds. More specifically, the present invention relates to novel thiophene compounds, processes for making such compounds, and their use, inter alia, as anesthetics, herbicides, and fungicides.

BACKGROUND OF THE INVENTION

The sodium channel is a transmembrane protein responsible for the voltage-dependent modulation of the sodium ion permeability of excitable membranes and thus plays an essential role in generating action potentials. Hille, B., *Ionic Channels of Excitable Membranes*, Sinauer, Sunderland, Mass. (1984). Propagation of the action potential in nerve and muscle cells is generally thought to occur by transient changes in the permeability of the cell membrane to $Na^+$ ions via a specific channel. Two events can be distinguished in the passage of $Na^+$ through the channel: 1) selective filtering and 2) rapid increase in the permeability to Na+ by a gating type of mechanism. Angelides, K. J. and T. J. Nuttov, *J. Biol. Chem.* 258:11858–11867 (1981). In addition, ion channels may be either voltage gated, implying that current is gated or regulated by membrane potential (voltage), or chemically gated (e.g., acetylcholine receptors and γ-aminobutyric acid receptors), implying that current is gated primarily by binding of a chemical rather than by the membrane potential. Butterworth, J. F. and G. R. Strichartz, *Anesthesiology* 72:711–734 (1980).

The pharmacology of sodium channels has been extensively studied. A variety of protein and nonprotein toxins are found to modify the physiology of sodium channels. At present, six different binding sites for toxins have been postulated. These include extracellular surface sites for tetrodotoxin and for two different classes of peptide toxins (α and β, usually isolated from scorpion venoms), intramembranous sites for three classes of lipophilic organic molecules (brevetoxin/ciguatoxin and the classical activators such as batrachotoxin and veratridine, and certain synthetic insecticides), and the site(s) of local anesthetics action. Each of these sites appears to be linked to at least one other site, via conformationally coupled interactions that often are dependent on the membrane potential. Butterworth, J. T. and G. R. Strichartz, *Anesthesiology*, 72:711–734 (1990).

Local anesthetics are a class of chemical compounds that reversibly block the peripheral and central nerve pathways following regional administration. The actual site of local anesthetic molecular action is the sodium channel membrane pore which regulates ion influx. The neuroreceptor site in the pore must have the ability to undergo conformational change from a closed to an open configuration to accommodate rapid changes in membrane potential. Local anesthetics are further classified as short, moderate or long acting agents depending on their capability and duration in time to block the sodium channels.

Paresthesia is a rare clinical finding subsequent to oral surgery accompanied by the administration of local anesthetics. Paresthesia can be defined as an altered sensation of numbness, burning or prickling that may reflect an alteration in the sensation of pain in the distribution of a specific sensory nerve. Patients who demonstrate such symptoms after surgery frequently suffer neurotoxicity which may be explained by the interaction of anesthetic metabolites with a specific neuroreceptor that is presumably responsible for the transmission of sensory nerve impulse. Specifically, there is a possible metabolic pathway for the breakdown of the local anesthetic molecule at the site of injection which would lead to the formation of an alcohol. See Nickel, A. A., *Aneth. Prog.* 37:42–45 (1990); Nickel, A. A., *Dentoalveolar Surgery* 5(1):17–24 (1993). It is now believed by the present inventor that in those patients with ion channel problems, this alcohol metabolite can remain bound to the alpha helix of the ion channel, stabilizing it in its closed conformation and thereby preventing the normal functioning of the channels (transport of the ions). Thus, paresthesia may be due to sodium channel dysfunction in these patients.

Various anesthetics are known in the art. For example, N-substituted glycine anilide, prilocaine, tetracaine, butanilicaine, trimecaine, bensocaine, lidocaine, bupivacaine, dibucaine, mepivacaine and etidocaine have been described as having useful anesthetic properties. See generally, U.S. Pat. Nos. 4,069,105, 4,562,060. Further, certain lidocaine and thiophene derivatives have also been described (e.g. U.S. Pat. No. 4,891,386 (describing lidocaine salicylate monohydrate); U.S. Pat. No. 5,166,346 (describing certain thiophene derivatives); U.S. Pat. No. 3,855,243 (describing 3-aminoacylamino thiophenes)).

With the exception of articaine and bucricane, (which are not yet approved by the Food and Drug Administration for use within the United States) all local anesthetics in use today are derived from anilines. Two recent studies indicate that one of the most widely used local anesthetics, lidocaine, is metabolically hydrolyzed in the body with the resultant release of an aniline homolog of carcinogenic potential. The Food And Drug Administration's Center for Drug Evaluation and Research Pilot Drug Staff, Anesthetic and Life Support Drugs Advisory Committee, was presented evidence on Jun. 10, 1994, that lidocaine is converted into an aniline homolog, 2, 6-xylidine, an established animal and probable human carcinogen. In the second study, human serum hemoglobin adduct from cardiac patients demonstrated high levels of 2,6-xylidine after routine therapeutic administration of lidocaine. Bryant, et al., *Carcinogenesis* 15(10): 2287–2290; 1994. Significantly, 2,6-xylidine is an established animal carcinogen. National Toxicology Program No. 278, NIH Pub. No. 90-2534, January, 1990. Additionally, a metabolite of the aniline-derived anesthetic prilocane, ortho-toluidine hydrochloride, has also been found carcinogenic in rats and mice. US Department of HHS, *Sixth Annual Report on Carcinogens, National Toxicology Program Vol.* 2, pp. 775–77 (1991); Hechl et al., *Cancer Lett.* 16:103–08 (1982); Weisburger et al., *J. Environ. Pathol. Toxicol.* 2:325–56 (1978).

Although individual studies of each aniline local anesthetic have not been done, it is reasonable to expect that all aniline local anesthetics are metabolized to release their aniline homologs into the body. Therefore, these aniline based anesthetics may induce diseases related to sodium channel dysfunction, including paresthesia as well as cancer.

As most of today's commercially used anesthetics are aniline based compounds, it is desirable to identify sodium channel active molecules having anesthesia-like properties that do not induce diseases related to sodium channel dysfunction. Additionally, since a single anesthetic may not be ideal in all applications, it is desirable to develop a variety of molecules which vary in onset, duration, and profundity of anesthesia. It is further desirable to identify a method for identifying such molecules.

SUMMARY OF THE INVENTION

The present invention is directed to novel sodium channel active compounds. The compounds of the invention are capable of interacting and affecting the normal function of sodium channel and may be used as an anesthetic. These molecules have a binding site on sodium channels which is directly or indirectly linked with the binding site of a local anesthetic such as lidocaine. The preferred compounds of the invention are selected from the group comprising thiophenes and more specifically, ester and amide thiophenes and their derivatives and salts. These novel thiophene local anesthetics have been designed to parallel the action of the currently used aniline local anesthetics by substituting a thiophene ring in place of the benzyl group in the aniline derivative compounds.

In accordance with one aspect of the invention, the thiophene compound is an ester of the following formula:

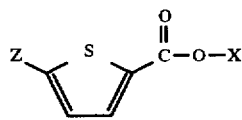

wherein:

X is —CH$_2$N (C$_2$H$_5$)$_2$; —CH$_2$N (CH$_3$)$_2$; —CH(CH$_3$)NH (C$_3$H$_7$); or Y; and Y is selected from the group comprising:

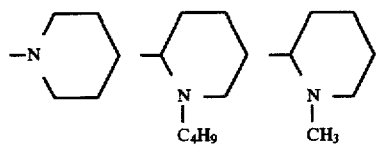

or its salt;

and Z is an alkylamino radical or preferably NH$_2$.

In accordance with another aspect of the invention, the preferred compound is a saturated amide thiophene of the formula:

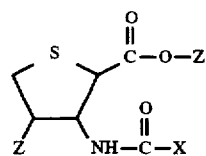

wherein X is —CH(CH$_3$)NHC$_2$H$_5$; —C(CH$_3$)$_2$N(C$_2$H$_5$)$_2$; or —CH(CH$_3$)Y; and Y is selected from the group comprising:

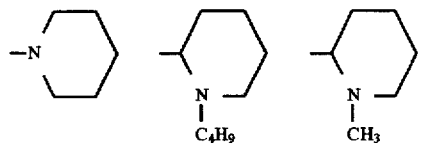

or its salt, and Z is a short chain alkyl group.

In accordance with a still further aspect of the invention, the thiophene compound is an unsaturated amide thiophene of the formula:

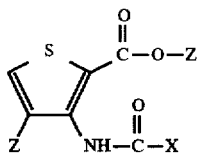

wherein X is —CH(CH$_3$)NHC$_2$H$_5$; —C(CH$_3$)$_2$N(C$_2$H$_5$)$_2$; or —CH(CH$_3$)Y; and Y is selected from the group comprising:

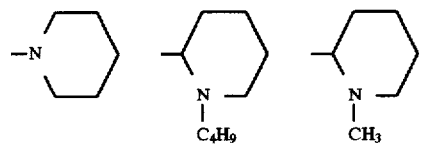

or its salt, and Z is a short chain alkyl group.

Still another aspect of this invention is a process for the preparation of a thiophene derivative by reacting a nitro-thiophene-2-carboxylic acid with an amino alcohol, reducing the resulting product into an amino-thiophene-ester, and reacting the reduced compound with

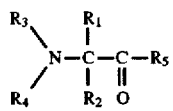

wherein R$_1$ and R$_2$ are H or a C$_1$ to C$_4$ alkyl group, R$_3$ and R$_4$ are organic radicals or, together with the N atom to which they are attached form a ring comprised of 3 or 4 carbons, or alternatively, R$_2$ and R$_4$ may also be linked together in a contiguous alkyl chain to form a ring comprised of 3 or 4 carbons, and R$_5$ is OH, Br, or Cl.

The present invention is further directed towards the use of these compounds as local anesthetics. A still further aspect of the present invention is the use of these compounds as herbicides and fungicides.

DEFINITION OF TERMS

For the purpose of clarity, the following terms are defined and so used in the present invention:

(1) Circular dichroism (CD) is an absorptive phenomenon that results when a chromophore interacts with plane polarized light at a specific wavelength. The absorption band can be either negative or positive depending on the differential absorption of the right and left circularly polarized components for that chromophore. Unlike optical rotatory dispersion (ORD) that measures the contributions of background and the chromophore of interest many millimicrons from the region of actual light interaction, circular dichroism offers the advantage of measuring optical events at the wavelength at which the event takes place. Circular dichroism, then, is specific to the electronic transition of the chromophore. Beychok, S., *Science* 154:1288–1289 (1966).

(2) Neuroreceptor—neuroreceptor is a macromolecule generally associated with the nervous system and has specific binding sites for the recognition of a series of ligands and the binding of said ligands to the macromolecule will induce a neurophysiological response.

(3) Molar ellipticity—molar ellipticity is a unit used by the present invention to express the transitional activity of a given conformation at a specific wavelength.

(4) Short chain alkyl group—a short chain alkyl group is an alkyl radical comprised of 1 to 8 carbon atoms which may form a linear or branched structure. Preferably, a short chain alkyl group is a methyl group.

BRIEF DESCRIPTION OF THE DRAWINGS

The following is a brief description of the drawings. More detailed descriptions of the drawings are found in the Example section of this specification.

DETAILED DESCRIPTION OF THE INVENTION

Figure 1:
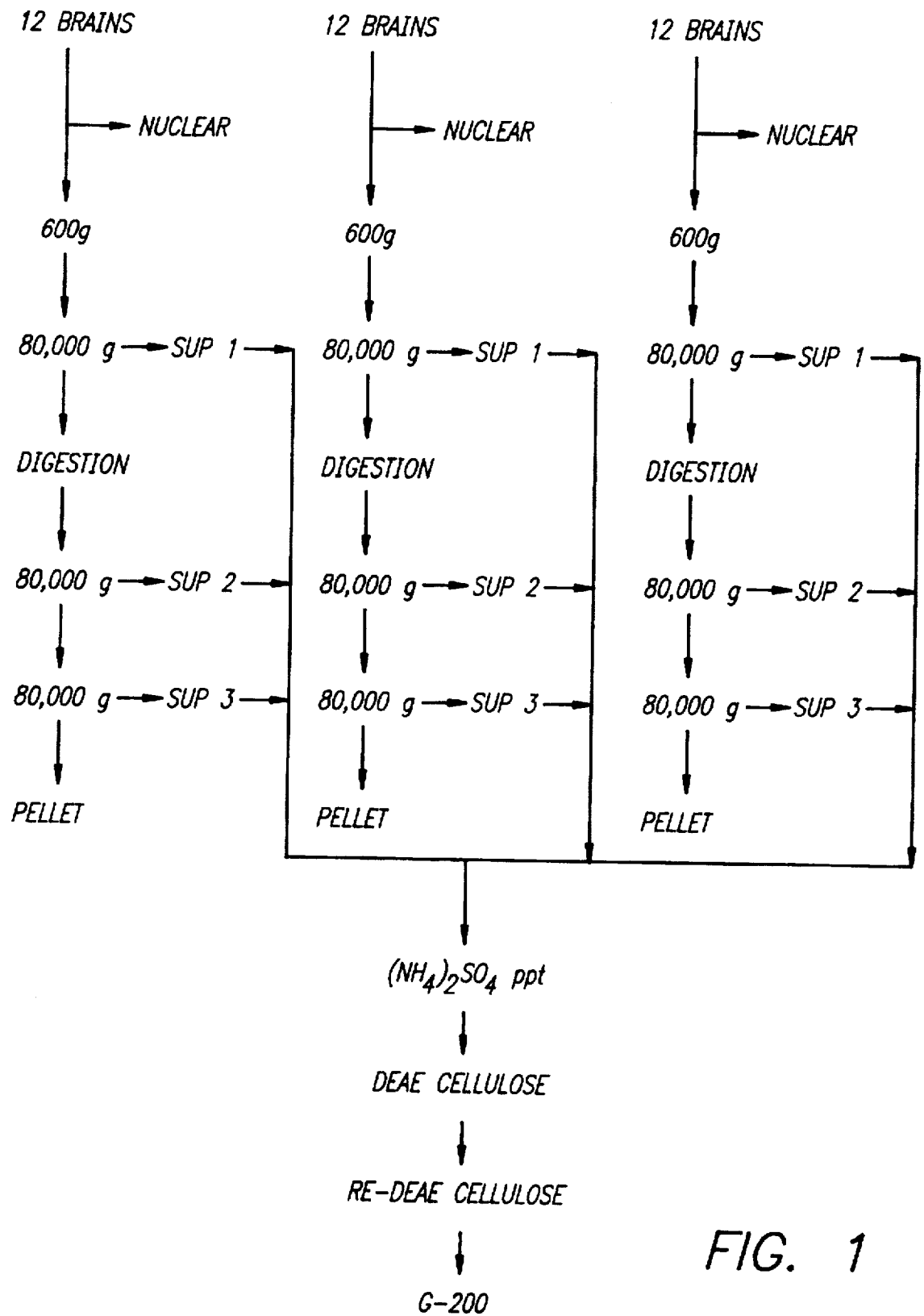
FIG. 1 is the outline of the experimental procedures for the preparation, isolation and purification of neuroreceptors from beef brains.

A. Sodium Channel Active Compounds and Their Synthesis

The present invention is directed to novel ester thiophene compounds. For the most part, the compounds are ester thiophenes having the following general formula:

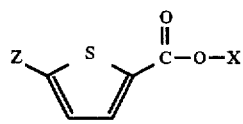

wherein:

X is —CH$_2$N(C$_2$H$_5$)$_2$; —CH$_2$N(CH$_3$)$_2$; —CH(CH$_3$)NH (C$_3$H$_7$); or Y; and Y is selected from the group comprising:

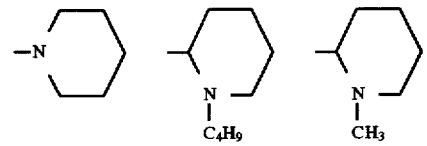

and Z is an alkylamino radical or preferably NH$_2$.

These compounds may be synthesized by a number of processes, including:

a. 5-nitro-thiophene-2-carboxylic acid, synthesized according to Sy and deMalleray, *Bull. Soc. Chim.*, France (1963) at 1276 or Gever, *J. Am. Chem. Soc.* 77:577 (1955) and Mackay, *Can. J. Chem.* 44:2881 (1966);

b. is reacted with XOH, wherein:
X is —CH$_2$N(C$_2$H$_5$)$_2$; —CH$_2$N(CH$_3$)$_2$; —CH (CH$_3$) NH(C$_3$H$_7$); or Y; and Y is selected from the group comprising:

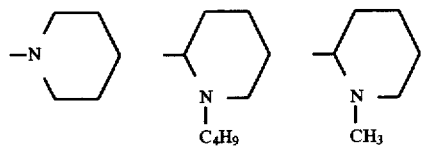

or any other known amino alcohol, into a 5-nitro-thiophene-ester;

c. said 5-nitro-thiophene-ester is then reduced (Al$^{+1}$/Hg$^+$$_1$) by any known method into 5-amino-thiophene-ester;

d. and reacting the reduced compound with

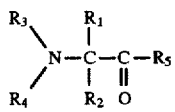

wherein R$_1$ and R$_2$ are H or a C$_1$ to C$_4$ alkyl group, R$_3$ and R$_4$ are organic radicals or, together with the N atom to which they are attached form a ring comprised of 3 or 4 carbons, or alternatively, R$_2$ and R$_4$ may also be linked together in a contiguous alkyl chain to form a ring comprised of 3 or 4 carbons, and R$_5$ is OH, Br, or Cl.

Alternatively, the novel compounds are saturated amide thiophenes having the general formula:

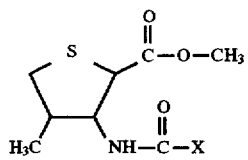

wherein:

X is —CH(CH$_3$)NHC$_2$H$_5$; -C(CH$_3$)$_2$N(C$_2$H$_5$)$_2$; or —CH (CH$_3$)Y; and Y is selected from the group comprising:

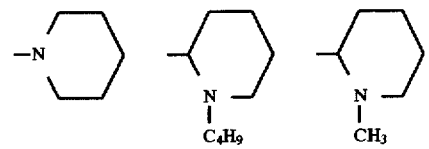

Alternatively, the novel compounds are unsaturated amide thiophenes having the general formula:

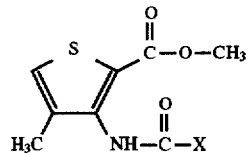

wherein:

X is —CH(CH$_3$)NHC$_2$H$_5$; —C(CH$_3$)$_2$N(C$_2$H$_5$)$_2$; or —CH(CH$_3$)Y; and Y is selected from the group comprising:

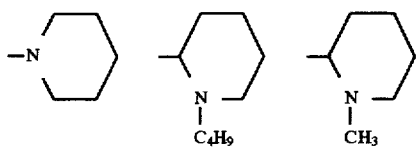

Significantly, these compounds differ from those disclosed specifically in U.S. Pat. No. 3,855,243 in that the alkylene in the aminoacylamino is sterically hindered. These structural differences are designed to affect the extent and the time of duration of the action of these compounds on the sodium channel.

These compounds may be synthesized by a number of processes, including:

a. the known thiophene ester 3-amino-2-methoxycarbonyl-4-methyl thiophene

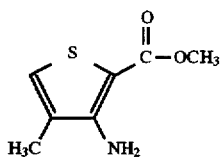

b. is reacted with

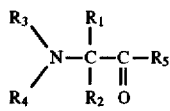

wherein $R_1$ and $R_2$ are H or a $C_1$ to $C_4$ alkyl group, $R_3$ and $R_4$ are organic radicals, preferably an H or an alkyl group, or, together with the N atom to which they are attached form a ring, and $R_5$ is OH, Br, or Cl. $R_2$ and $R_4$ may also be linked together in a contiguous alkyl chain to form a ring comprised of 3 or 4 carbons.

Additionally, the compounds of the invention may be synthesized by one skilled in the art using well known synthetic organic chemistry reactions and mechanisms such as those taught in Tatchell et al., *Vogel's Textbook of Practical Organic Chemistry*, 5th ed., John Wiley & Sons, NY (1989), and March, J., *Advanced Organic Chemistry— Reactions, Mechanisms and Structures*, 4th ed., John Wiley & Sons, NY (1992), both of which are incorporated herein by reference. Part of the synthesis strategies may depend on protective groups. Suitable protecting groups will depend on the functionality and particular chemistry used to construct the compounds of the invention. Examples of suitable functional groups will be readily apparent to skilled artisans, and are described, for example, in Greene and Wutz, *Protecting Groups in Organic Synthesis*, 2d ed., John Wiley & Sons, NY (1991), which is incorporated herein by reference.

B. Toxicity Profile of Compounds

Thiophene has been tested generally in Salmonella assays to determine whether thiophene-based compounds are likely to induce gene mutations. As set forth below in Example 5, the toxicities of the compounds of the present invention are believed to be of the same order as those of disclosed, non-novel thiophene compounds.

C. Pharmaceutical Formulations and Routes of Administration

The identified ester and amide thiophene compounds can be administered to a patient, by itself, or in pharmaceutical compositions where it is mixed with suitable carriers or excipient(s) at therapeutically effective doses for use as an anesthesia. A therapeutically effective dose refers to that amount of the compound sufficient to result in a clinical anesthetic effect.

Compositions for use in accordance with the present invention may be formulated in any conventional manner using one or more physiologically acceptable carriers or excipients.

Techniques for formulation and administration may be found in "Remington's Pharmaceutical Sciences," Mack Publishing Co., Easton, Pa., latest edition. Suitable routes may, for example, include topical, oral, rectal, transmucosal, or intestinal administration; parenteral delivery, including intramuscular, subcutaneous, intramedullary injections, as well as intrathecal, direct intraventricular, intravenous, intraperitoneal, intranasal, or intraocular injections. For injection, the agents of the invention may be formulated in aqueous solutions, preferably in physiologically compatible buffers such as Hanks's solution, Ringer's solution, or physiological saline buffer. For transmucosal administration, penetrants appropriate to the barrier to be permeated are used in the formulation. Such penetrants are generally known in the art.

The compounds can be formulated readily using pharmaceutically acceptable carriers well known in the art into dosages suitable for oral and/or topical administration. Such carriers enable the compounds of the invention to be formulated as tablets, pills, capsules, liquids, gels, syrups, slurries, suspensions and the like, for oral ingestion by a patient to be treated. Alternatively, the compound can be formulated as, for example, creams and lotions for topical administration to a patient to be treated.

Compositions suitable for use in the present invention include compositions wherein the active ingredients are contained in an effective amount to achieve its intended purpose. Determination of the effective amounts is well within the capability of those skilled in the art, especially in light of the detailed disclosure provided herein.

In addition to the active ingredients these compositions may contain suitable pharmaceutically acceptable carriers comprising excipients and auxiliaries which facilitate processing of the active compounds into preparations which can be used pharmaceutically. The preparations formulated for oral administration may be in the form of tablets, dragees, capsules, or solutions. The preparations formulated for topical administration may be in the form of lotions, creams and oils.

The compositions of the present invention may be manufactured in a manner that is itself known, e.g., by means of conventional mixing, dissolving, granulating, dragee-making, levigating, emulsifying, encapsulating, entrapping or lyophilizing processes.

Preparations for oral use can be obtained by combining the active compounds with solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added.

For buccal administration, the compositions may take the form of tablets or lozenges formulated in conventional manner.

The compounds may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Formulations for parenteral administration include aqueous solutions of the active compounds in water-soluble form. The compounds of the invention may be formulated in water or in an aqueous saline or salt solution. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active ingredient may be in powder form for constitution with a suitable vehicle, e.g., sterile pyrogen-free water, before use.

The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt.

The compositions may, if desired, be presented in a pack or dispenser device which may contain one or more unit dosage forms containing the active ingredient. The pack may for example comprise metal or plastic foil, such as a blister pack. The pack may also, for example, be in the form of a plastic-type flexible container where the composition is in the form of a lotion or cream. The pack or dispenser device may be accompanied by instructions for administration. Compositions comprising a compound of the invention formulated in a compatible pharmaceutical carrier may also be prepared, placed in an appropriate container, and labelled for treatment of an indicated condition.

A carrier for the compounds of the invention may be a cosolvent system comprising benzyl alcohol, a nonpolar surfactant, a water-miscible organic polymer, and an aqueous phase. A preferred cosolvent system is the VPD co-solvent system. VPD is a solution of 3% w/v benzyl alcohol, 8% w/v of the nonpolar surfactant polysorbate 80, and 65% w/v polyethylene glycol 300, made up to volume in absolute ethanol. The VPD co-solvent system (VPD:5W) consists of VPD diluted 1:1 with a 5% dextrose in water solution. This co-solvent system dissolves hydrophobic compounds well, and itself produces low toxicity upon systemic administration. Naturally, the proportions of a co-solvent system may be varied considerably without destroying its solubility and toxicity characteristics. Furthermore, the identity of the co-solvent components may be varied: for example, other low-toxicity nonpolar surfactants may be used instead of polysorbate 80; the fraction size of polyethylene glycol may be varied; other biocompatible polymers may replace polyethylene glycol, e.g. polyvinyl pyrrolidone; and other sugars or polysaccharides may substitute for dextrose.

Alternatively, other delivery systems for the claimed compounds may be employed. Liposomes and emulsions are well known examples of delivery vehicles or carriers for hydrophobic drugs. Certain organic solvents such as DMSO also may be employed, although usually at the cost of greater toxicity.

The compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Many of the sodium ion channel modulating compounds of the invention may be provided as salts with pharmaceutically compatible counterions. Pharmaceutically compatible salts may be formed with many acids, including but not limited to hydrochloric, sulfuric, acetic, lactic, tartaric, malic, succinic, etc. Salts tend to be more soluble in aqueous or other protonic solvents that are the corresponding free base forms.

The composition or formulation to be administered will, in any event, contain such quantity of the compositions that will assure that a therapeutically effective amount will be delivered to a patient. A therapeutically effective amount means an amount effective to obtain the desired anesthetic effect. The exact formulation, route of administration and dosage can be chosen by an individual physician in view of a patient's condition (see e.g., Fingl et al., 1975, "The Pharmacological Basis of Therapeutics," Chapt. 1, p.1).

Dosage amount and interval may be adjusted individually to provide plasma levels of the active moiety which are sufficient to maintain anesthesia effects.

Dosage amount and interval may be adjusted individually to provide plasma levels of the active moiety which are sufficient to maintain the anesthetic effects. Usual average plasma levels should be maintained within 50–5000 µg/ml, commonly 50–1000 µg/ml, and typically 100–500 µg/ml In cases of local administration or selective uptake, the effective local concentration of the drug may not be related to plasma concentration.

The amount of composition administered will, of course, be dependent on the subject being treated, on the subject's weight, the severity of the affliction, the manner of administration and the judgment of the prescribing physician.

D. Formulations for Use as a Fungicide or Herbicide

The compounds of this invention will generally be used in formulation with a liquid or solid diluent or with an organic solvent. The formulations may further comprise additional compounds that have fungicidal or herbicidal activity. Useful formulations of the compound of the invention can be prepared in conventional ways. They include dusts, granules, pellets, solutions, emulsions, wettable powders, emulsifiable concentrates and the like. Many of these may be applied directly. Sprayable formulations can be extended in suitable media and used at spray volumes of from about one to several hundred liters per hectare. High strength compositions are primarily used as intermediates for further formulation. The formulations, broadly, contain about 1% to 99% by weight of active ingredient(s) and at least one of a) about 0.1% to 35% surfactant(s) and b) about 5% to 99% solid or liquid inert diluent(s).

Lower or higher levels of active ingredient can, of course, be present depending on the intended use and the physical properties of the compound. Higher ratios of surfactant to active ingredient are sometimes desirable, and are achieved by incorporation into the formulation or by tank mixing.

Typical solid diluents are described in Watkins et al., "Handbook of Insecticide Dust Diluents and Carriers," 2nd Ed., Dorland Books, Caldwell, N.J. The more absorptive diluents are preferred for the wettable powders and the denser ones for dusts. Typical liquid diluents and solvents are described in Marsden, "Solvents Guide," 2nd Ed., Interscience, New York, N.Y., 1950. Solubility under 0.1% is preferred for suspension concentrates; solution concentrates are preferably stable against phase separation at 0° C. "McCutcheon's Detergents and Emulsifiers Annual," MC Publishing Corp., Ridgewood, N.J., as well as Sisely and Wood, "Encyclopedia of Surface Active Agents," Chemical Publ. Co., Inc., New York, N.Y., 1964, list surfactants and recommended uses. All formulations can contain minor amounts of additives to reduce foam, caking, corrosion, microbiological growth, etc. Additives to protect the active compounds against light induced degradation, e.g., photoprotectants, UV screening compounds, and the like are also preferably included in the subject formulations. Preferably, ingredients should be approved by the U.S. Environmental Protection Agency for the use intended.

The methods of making such compositions are well known. Solutions are prepared by simply mixing the ingredients. Fine solid compositions are made by blending and, usually, grinding as in a hammer or fluid energy mill. Suspensions are prepared by wet milling (see, for example, Littler, U.S. Pat. No. 3,060,084). Granules and pellets may be made by spraying the active material upon preformed granular carriers or by agglomeration techniques. See J. E. Browning, "Agglomeration," Chemical Engineering, Dec. 4, 1967, pp. 147ff and "Perry's Chemical Engineer's Handbook," 4th Ed., McGraw-Hill, New York, N.Y., 1963, pp. 8–59ff.

For more information regarding the art of formulation, see for example:

H. M. Loux, U.S. Pat. No. 3,235,361, Feb. 15, 1966, Column 6, Line 16 through Column 7, Line 19 and Examples 10 through 41.

R. W. Luckenbaugh, U.S. Pat. No. 3,309,192, Mar. 14, 1967, Column 5, Line 43 through Column 7, Line 62 and Examples 8, 12, 15, 39, 41, 52, 53, 58, 132, 138–140, 162–164, 166, 167, 169–182.

H. Gysin and E. Knusli, U.S. Pat. No. 2,891,855, Jun. 23, 1959, Column 3, Line 66 through Column 5, Line 17 and Examples 1–4.

G. C. Klingman, "Weed Control as a Science," John Wiley and Sons, Inc., New York, N.Y., 1961, pp.81–96.

J. D. Fryer and S. A. Evans, "Weed Control Handbook," 5th Ed. Blackwell Scientific Publications, Oxford, 1968, pp. 101–103.

The following examples serve to illustrate the invention without, however, limiting the latter.

EXAMPLE 1

Preparation of an Ester Thiophene a) 5-nitrothiophene-2-carboxylic acid (prepared according to Sy and deMalleray, Bull. Soc. Chim., France (1963) at 1276 or Gever, J. Am. Chem. Soc. 77:577 (1955) and Mackay, Can. J. Chem. 44:2881 (1966)) is esterified with the amino alcohol $N(CH_3)_2CH_2OH$ to form the nitro ester:

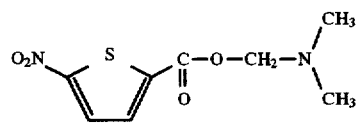

which is then reduced by known means (such as hydrogenation in the presence of a reducing metal such as Ni or Co) to the analogous 5-amino-thiophene ester:

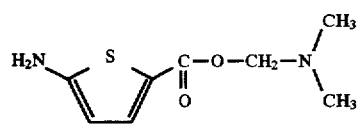

b) In a similar manner, the 5-nitrothiophene-2-carboxylic acid is esterified with one of the following amino alcohols: $N(C_2H_5)_2CH_2OH$; $NH(C_3H_7)CH(CH_3)OH$; or YOH, wherein Y is selected from the group comprising:

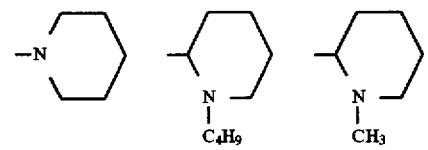

c) Alternatively, an alcohol such as ethanol is used to esterify the carboxylic acid group.

EXAMPLE 2

Preparation of 5-Dialkylaminoalkylamido-thiophene-2-carboxylate esters a) The thiophene ester 2-ethoxycarbonyl-5-amino thiophene is reacted with $CO_2HCHCH_3NHC_2H_5$ to give the compound:

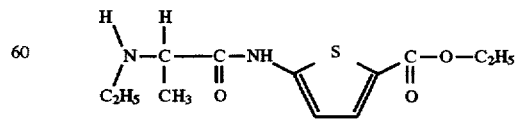

b) In an analogous manner, the thiophene ester is reacted with one of the following amino alcohols or their derivatives: $CO_2HC(CH_3)_2N(C_2H_5)_2$; $CO_2HCHCH_3N(C_5H_{10})$;

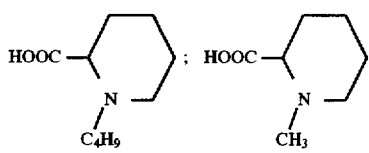

wherein the amino group on the thiophene ring forms the analogous amide derivative.

EXAMPLE 3

Preparation of Amide Thiophenes a) The known thiophene ester 3-amino-2-methoxycarbonyl-4-methyl thiophene:

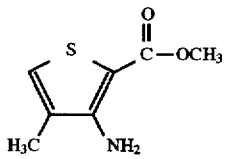

is reacted with $CO_2HCHCH_3NHC_2H_5$ to give the amide thiophene compound:

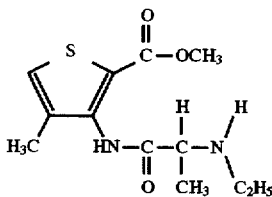

b) In an analogous manner, the thiophene ester is reacted with one of the following amino alcohols or their derivatives: $CO_2HC(CH_3)_2N(C_2H_5)_2$; $CO_2HCHCH_3N$ $(C_5H_{10})$;

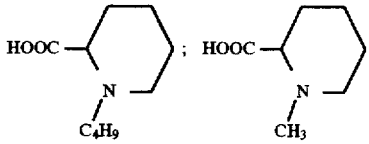

wherein the analogous amide thiophene compound is formed.

EXAMPLE 4

Toxicity Studies of Thiophene

Genetic toxicity studies of thiophene in a Salmonella assay were conducted by Zeiger, et al., *Environ. Mutagen.* 9(Suppl. 9):1–109.

A. Salmonella Assay Protocol

The Salmonella assay was performed according to the protocol generally described in Haworth, et al. *Environ. Mutagen.* 5(Suppl. 1):3–142 (1983), with the following modification to the preincubation step. Thiophene was incubated with the tester strain either in buffer or S9 plus cofactor mix for 20 minutes at 37° C. prior to the addition of soft agar and plating on minimal agar plates.

Thiophene was tested both in the presence and absence of metabolic activation from Aroclor 1254-induced Sprague-Dawley rats and Syrian hamsters, in Salmonella strains TA98, TA100, TA1535 and TA97. When tested in series, all negatives are repeated. All positives are repeated for conditions that elicited the positive response. When tested as a hierarchy, thiophene was tested initially in TA100 and TA98 and repeated if positive. If negative, the thiophene was then tested in TA 1535 and TA 97. If still negative, all strains were retested with a change in the S9 concentration.

Each test consists of triplicate plating of concurrent positive and solvent controls and of at least 5 doses of test chemical; the high dose is limited by toxicity or solubility, but not exceeding 10 mg/plate. A positive response is defined as a reproducible, dose related increase in histidine-independent (revertant) colonies. An equivocal response is either a non-dose-related increase or a response that is not reproducible. A chemical is judged positive if a reproducible positive response is observed in any strain/activation combination.

B. Experimental Results

The following results were observed:

| Dose | 1 NA (–) | | 2 NA (–) | | 1 10% HLI (–) | | 1 30% HLI (–) | | 1 10% RLI (–) | | 1 30% RLI (–) | |
|---|---|---|---|---|---|---|---|---|---|---|---|---|
| ug/plate | mean | SE | mean | SE | mean | SE | mean | SE | mean | SE | mean | SE |
| For Strain TA100, in DMSO solvent | | | | | | | | | | | | |
| 0.000 | 143 | 4.5 | 93 | 6.4 | 94 | 4.3 | 112 | 4.5 | 141 | 6.5 | 117 | 9.4 |
| 10.000 | | | 97 | 5.2 | | | 92 | 4.9 | | | 111 | 6.9 |
| 33.000 | 122 | 1.2 | 103 | 13.4 | 89 | 4.3 | 109 | 8.7 | 128 | 2.5 | 106 | 9.6 |
| 100.000 | 128 | 7.2 | 102 | 8.3 | 103 | 10.8 | 102 | 7.3 | 137 | 4.9 | 111 | 10.7 |
| 333.000 | 103 | 3.3 | 103 | 9.6 | 105 | 7.4 | 104 | 2.6 | 129 | 16.1 | 92 | 1.8 |
| 1000.000 | 130 | 10.1 | 98 | 4.8 | 103 | 1.5 | 110 | 6.4 | 134 | 3.8 | 116 | 7.0 |
| 2000.000 | 88s | 6.7 | | | 85s | 6.2 | | | 103a | 10.3 | | |
| POS | 1386 | 57.2 | 759 | 17.8 | 1189 | 5.8 | 892 | 18.6 | 1501 | 31.2 | 640 | 32.9 |
| For Strain TA1535, in DMSO solvent | | | | | | | | | | | | |
| 0.000 | 41 | 2.3 | 28 | 3.3 | 12 | 1.2 | 10 | 0.6 | 29 | 5.2 | 14 | 1.7 |
| 10.000 | | | 31 | 2.8 | | | 10 | 2.4 | | | 16 | 0.3 |

-continued

| Dose ug/plate | 1 NA (-) mean | SE | 2 NA (-) mean | SE | 1 10% HLI (-) mean | SE | 1 30% HLI (-) mean | SE | 1 10% RLI (-) mean | SE | 1 30% RLI (-) mean | SE |
|---|---|---|---|---|---|---|---|---|---|---|---|---|
| 33.000 | 32 | 1.5 | 32 | 2.3 | 13 | 1.2 | 12 | 2.2 | 33 | 3.5 | 14 | 0.6 |
| 100.000 | 33 | 5.2 | 28 | 0.3 | 18 | 3.2 | 13 | 1.3 | 33 | 1.8 | 16 | 2.2 |
| 333.000 | 32 | 4.7 | 30 | 1.9 | 13 | 3.3 | 12 | 1.2 | 34 | 5.7 | 12 | 1.5 |
| 1000.000 | 32 | 2.7 |  |  | 13 | 0.0 | 12 | 1.5 | 28 | 3.2 | 10 | 3.8 |
| 2000.000 | 23a | 3.2 |  |  | 9a | 1.5 |  |  | 27a | 0.7 |  |  |
| POS | 1057 | 34.2 | 609 | 32.5 | 160 | 7.1 | 220 | 17.9 | 152 | 3.0 | 165 | 5.2 |

For Strain TA97, in DMSO solvent

| 0.000 | 99 | 5.3 | 92 | 0.6 | 134 | 2.7 | 139 | 9.3 | 110 | 5.9 | 178 | 5.2 |
| 10.000 |  |  | 104 | 0.9 |  |  | 141 | 10.4 |  |  | 186 | 4.2 |
| 33.000 | 103 | 3.8 | 115 | 5.2 | 127 | 13.1 | 147 | 7.8 | 125 | 4.9 | 196 | 4.5 |
| 100.000 | 103 | 1.7 | 98 | 4.1 | 140 | 0.3 | 142 | 4.7 | 119 | 0.7 | 204 | 8.1 |
| 333.000 | 107 | 7.3 | 104 | 6.5 | 132 | 4.7 | 137 | 2.9 | 117 | 7.2 | 194 | 6.9 |
| 1000.000 | 86 | 6.6 | 98 | 3.8 | 113 | 8.8 | 144 | 6.8 | 120 | 12.8 | 176 | 6.1 |
| 2000.000 | 84s | 5.5 |  |  | 113a | 12.9 |  |  | 100a | 2.6 |  |  |
| POS | 698 | 17.4 | 600 | 11.3 | 605 | 11.9 | 540 | 25.8 | 791 | 23.2 | 537 | 6.9 |

For Strain TA98, in DMSO solvent

| 0.000 | 17 | 3.7 | 13 | 1.8 | 29 | 3.3 | 33 | 6.6 | 32 | 5.0 | 26 | 1.3 |
| 10.000 |  |  | 15 | 1.2 |  |  | 29 | 5.2 |  |  | 29 | 5.5 |
| 33.000 | 18 | 3.8 | 18 | 1.2 | 29 | 2.2 | 24 | 3.2 | 32 | 2.2 | 24 | 3.4 |
| 100.000 | 17 | 0.7 | 10 | 2.2 | 33 | 3.0 | 27 | 6.2 | 30 | 0.9 | 28 | 1.5 |
| 333.000 | 16 | 2.3 | 14 | 5.0 | 36 | 3.5 | 23 | 2.7 | 32 | 0.6 | 28 | 1.9 |
| 1000.000 | 23 | 3.0 | 16 | 1.5 | 30 | 4.0 | 21 | 2.3 | 35 | 2.9 | 28 | 2.7 |
| 2000.000 | 16s | 2.7 |  |  | 31a | 0.3 |  |  | 27a | 1.7 |  |  |
| POS | 1598 | 10.5 | 1447 | 23.5 | 1309 | 39.6 | 701 | 93.6 | 1693 | 45.5 | 576 | 22.1 |

The conclusion that can be drawn from these results is that thiophene does not function as a mutagen in this assay. Based on this data, it is expected that at anesthetic doses, the thiophene compounds of the invention would also exhibit no mutagenic effect.

C. In Vivo Toxicity of Thiophene

The following data on in vivo toxicity of thiophene were obtained from the National Toxicology Program study files NTP Prechronic Studies on Thiophene (CAS No. 110-02-1), personal communication from Drs. Fung and Eastin, NIH, NIEHS.

1. Rat Inhalation Assay

In addition to the in vitro Salmonella assay described above, Fischer rats of both sexes were exposed to thiophene vapors in inhalation chambers (six hours per day including the T90) on weekdays for a total of 12 exposures. All rats exposed to 8000 ppm died following one exposure. During the first week of the study, mortality also occurred in the 2000 and 4000 ppm male exposure groups. Clinical signs of toxicity at the 4000 ppm exposure level included rough haircoat, ocular discharge, nasal discharge, dyspnea, and staggering gait. Thiophene exposure produced a dose-related depression in group mean body weight relative to control in rats of both sexes. Microscopic examination revealed chronic active inflammation of the lung in rats at the 4000 ppm exposure level and necrotizing inflammation of the liver in all exposure groups with severity increasing with dose. All dose groups of both sexes surviving until study termination showed a decrease in the absolute lung weight and in the lung to brain weight ratio.

2. Mice Inhalation Assay

B6C3FI mice of both sexes were exposed to thiophene vapors in wholebody inhalation exposure chambers (six hours per day including the T90) on weekdays for a total of 12 exposures. The exposure concentrations were 8000 ppm, 4000 ppm, 2000 ppm, 1000 ppm, 500 ppm, and 0 ppm thiophene. A base study group of five mice/sex/group was designated for necropsy and histopathologic evaluation and an additional five mice/sex/group were included in the study for special neuropathology evaluation.

Sex-related differences were exhibited in the survival data; the male mice at all thiophene exposure levels died or were terminated in moribund condition following a single exposure. Total mortality occurred in the females at the 8000 ppm and the 4000 ppm levels, while at the 2000 ppm level, 2/10 female mice died as a result of exposures. All female mice at the 1000 ppm and 500 ppm levels survived the study. Signs of toxicity seen in surviving mice at the 500 ppm and 1000 ppm levels included hypoactivity and abnormal posture while dyspnea also occurred at the 2000 ppm level. Thiophene exposure did not affect mean body weights or mean lung weights of the surviving female mice. However, liver absolute and relative organ weights (liver-to-body and liver-to-brain weight ratios) were increased relative to the controls, whereas, the thymus organ weight parameters were reduced. Microscopic pathology revealed that mortality was attributed to liver toxicity; centrilobular degeneration of hepatocytes occurred in mice that died early (within several hours after the first exposure) and centrilobular necrosis of hepatocytes occurred in surviving mice at all exposure levels. Necrotizing inflammation of the nose and nasal cavity was a second exposure-related lesion. This lesion was more severe in mice that survived the study than in mice that died after a single exposure. No other exposure-related microscopic lesions were found in the mice.

Thus, at extremely high inhalation doses, thiophene shows toxicity to liver and lung. However, this inventor notes that these exposures exceed the therapeutic dose by at least a thousand fold.

EXAMPLE 5

Toxicity Studies of Thiophene Derivative Compounds of the Invention

In a similar manner, the thiophene derivative compounds of the present invention are tested for toxicity in the Salmonella and both rat and mice inhalation protocols described above for thiophene. Likewise, they are expected to have a similar lack of toxicity at therapeutic doses because of their related chemical structure.

EXAMPLE 6

In Vivo Assay of Anesthetic Activity

The thiophene compounds of the invention are tested for their local anesthetic properties. Anesthetic activity by dermic infiltration is determined by the interdermic pompholyx method on the cutis of the back of the guinea-pig in accordance with Bulhring E. and Wajda F. "Biological comparison of local anesthetics", *J. Pharmacol. Exp. Ther.* 85:78–84 (1945). Three different concentrations of a thiophene derivative, as high as 10%, preferably up to 4%, most preferably 0.5%, 1%, and 1.5%, in a suitable carrier are injected into the animals. The number of negative responses to a set of six suitable stimulations at successive times after administering the drug is recorded. The thiophene derivative compounds of the invention are expected to have anesthetic activity which is perfectly reversible.

EXAMPLE 7

Circular Dichroism

As disclosed in PCT/US93/05792, published Jan. 6, 1994, one can identify compounds with potential analgesic effect by using circular dichroism to bioassay the interaction of molecules with ion channels, including sodium channels. Likewise, this bioassay technique is applicable to the thiophene compounds of the present invention.

To perform this method, solubilized nerve cell membrane proteins and acetylcholinesterase are purified using ion exchange and size exclusion chromatography. Then, one forms a mixture of a nerve cell protein and a compound capable of blocking or preventing the normal function of preferably the sodium channel in an excitable cell, and subjects that mixture to circular dichroism at a wave length of 222 nM wave length. The transition of molar ellipticity is measured while varying the temperature of the mixture between 25°–50° C. The transition of molar ellipticity of the mixture is compared with the transition of molar ellipticity of a control nerve cell protein without the compound capable of blocking or preventing the normal function of the sodium channel in an excitable cell. The alpha helix content, as measured at 222 nM, is used to monitor the effect of temperature change on the ion channel's conformational change.

Figure 2:
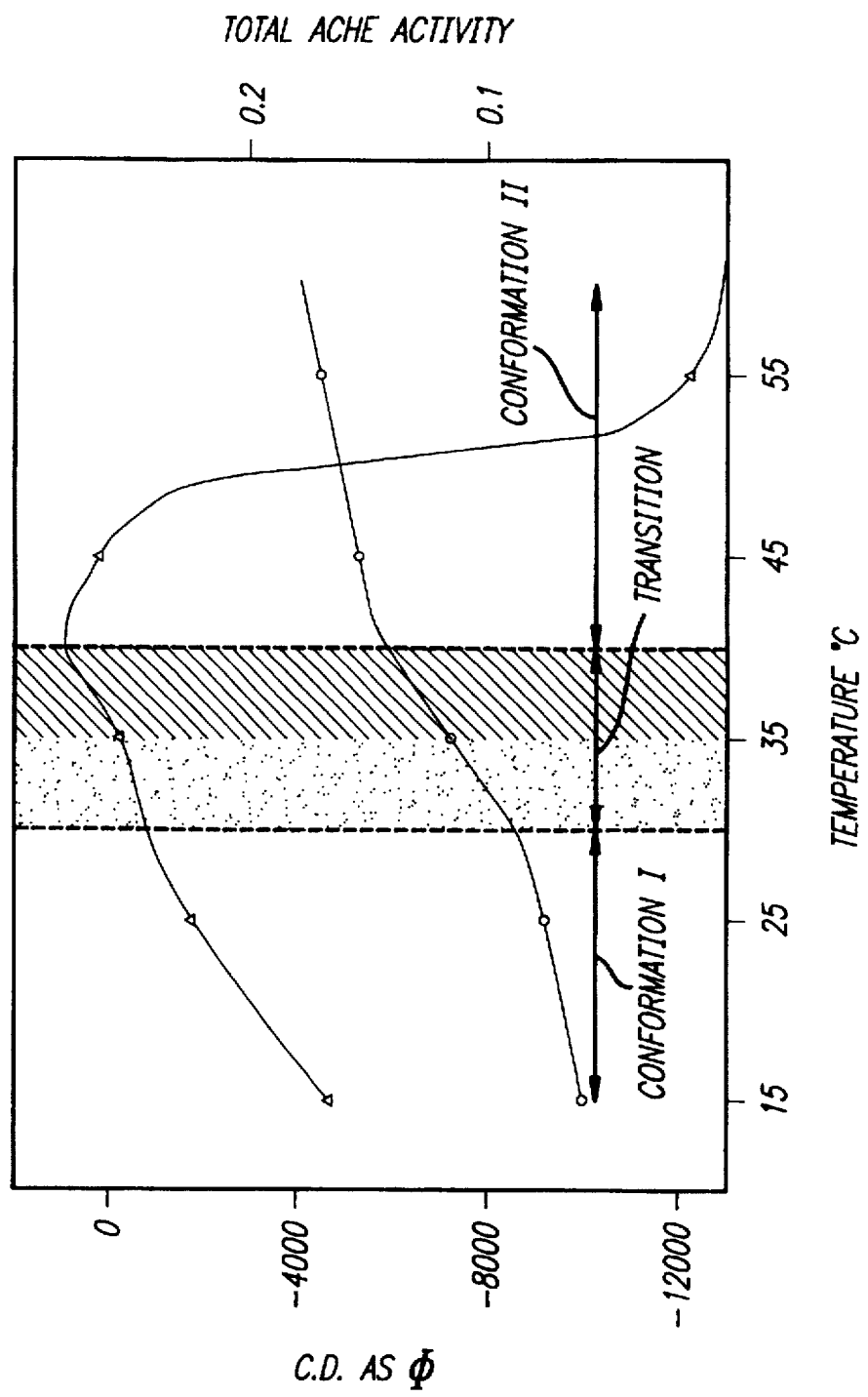
FIG. 2 presents the circular dichroism of sodium channel neuroreceptor at different temperature ranges. The activity of AChE is simultaneously measured to show that the helix-coil transition occurred without significant increase or decrease in enzyme activity.

In the absence of sodium channel active molecules, a sharp helical transition occurred in the temperature region near that of the bovine body temperature of 38.5° C. when bovine brain is the source of nerve cell membrane proteins. When the membrane protein preparation was monitored between a broader temperature range such as from 15° C. to 60° C., a gradual, but irreversible and endothermic helix-coil transition was observed between 30° C. and 40° C. (See FIG. 2). Simultaneous measurement of AChE activity gave a temperature dependent curve with a maximum of 37° C.–41° C., however, the helix-coil occurred without significant increase or decrease in enzyme activity. In addition, enzyme activity was rapidly lost at 55° C. without a significant change in helix content of the enzymes. It is suggested that the helix-coil transition observed between 30° C. to 40° C. is not due to the conformational change of AChE, but due to some other molecular component in the brain preparation that exhibits the observed helix-coil transition.

However, when a sodium channel active molecule is added to the membrane preparation, the temperature-dependent helix transition observed using circular dichroism is altered. Specifically the effect of lidocaine (a local anesthetic) and pilocarpine (an acetylcholine receptor agonist) on the helix-coil transition was studied in a beef brain nerve cell protein preparation at 222 nM between 15° C. to 60° C. The results are shown in TABLE 1 below. Surprisingly, both lidocaine and pilocarpine prevented the helical transition normally observed between 30°–35° C. in the absence of these compounds. These compounds, therefore, seem to stabilize the helix conformation of the sodium channel and to prevent the temperature-dependent uncoiling of alpha helix between 30° C.–35° C. When the temperature increases from 35° C. to 40° C., the alpha helix uncoils to equal the helix in the control sample.

TABLE 1

Percent Stabilization of Helical Conformation of AChE in the presence of Lidocaine and Pilocarpine

| Enzyme Conditions | % Loss of Helix (30° to 35° C.) | % Loss of Helix (35° to 40° C.) |
|---|---|---|
| Fresh AChE Control | 21.8 | 4.7 |
| Fresh AChE with Pilocarpine | 7.1 | 17.5 |
| Fresh AChE Control | 12.1 | 4.6 |
| Fresh AChE with Lidocaine | 1.8 | 13.6 |

Consequently, this method provides a unique bioassay technique that allows the screening of sodium channel active molecules with sodium channel by temperature-dependent circular dichroism. Bioassay, then, would be the testing of a new pharmaceutical against the purified mammalian neuroreceptor using circular dichroism to observe the results and the above described lidocaine test as the control.

The invention now being fully described, it will be apparent to one of ordinary skill in the art that many changes and modifications can be made thereto without departing from the spirit or scope of the invention as set forth herein.

What is claimed:

1. An ester thiophene of the formula:

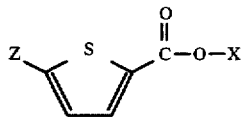

wherein:

X is —CH$_2$N(C$_2$H$_5$)$_2$; —CH$_2$N(CH$_3$)$_2$; and

Z is NH$_2$ or an alkylamino radical.

2. An anesthetic composition comprising the compound of claim 1.

3. A composition of claim 2 wherein the anesthetic is administered topically.

4. A method of anesthetizing a mammal comprising the step of administering the anesthetic composition of claim 2.

5. A fungicidal or herbicidal composition comprising the Compound of claim 1.

6. A fungicidal or herbicidal composition comprising an unsaturated amide thiophene of the formula:

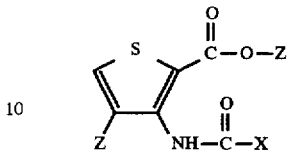

wherein:

X is —CH(CH$_3$)NHC$_2$H$_5$; or —C(CH$_3$)$_2$N(C$_2$H$_5$)$_2$; Z is a short chain alkyl group and a surfactant.

* * * * *